United States Patent [19]

Schumacher

[11] Patent Number: 5,358,404
[45] Date of Patent: Oct. 25, 1994

[54] APPARATUS FOR COMPRESSING AND ADAPTING FILLING MATERIAL

[76] Inventor: Dieter Schumacher, Beselerstr. 2, 2370 Rendsburg, Fed. Rep. of Germany

[21] Appl. No.: 46,278

[22] Filed: Apr. 12, 1993

[30] Foreign Application Priority Data

Apr. 14, 1992 [DE] Fed. Rep. of Germany ... 9205153[U]
Jun. 17, 1992 [DE] Fed. Rep. of Germany ....... 4219793

[51] Int. Cl.5 ............................................. A61C 3/06
[52] U.S. Cl. .................................................. 433/164
[58] Field of Search ......................................... 433/164

[56] References Cited

U.S. PATENT DOCUMENTS

| 246,981 | 9/1881 | Shumway | 433/164 |
| 532,720 | 1/1895 | Dennis | 433/164 |
| 532,721 | 1/1885 | Dennis | 433/164 |
| 4,586,901 | 5/1986 | Tanaka et al. | 433/164 |
| 5,030,093 | 7/1991 | Mitnick | 433/164 |

*Primary Examiner*—John J. Wilson
*Attorney, Agent, or Firm*—James E. Larson

[57] ABSTRACT

An apparatus for compressing and adapting filling material introduced into a dental cavity with an elastic punch which is fixed in or on a holder.

8 Claims, 2 Drawing Sheets

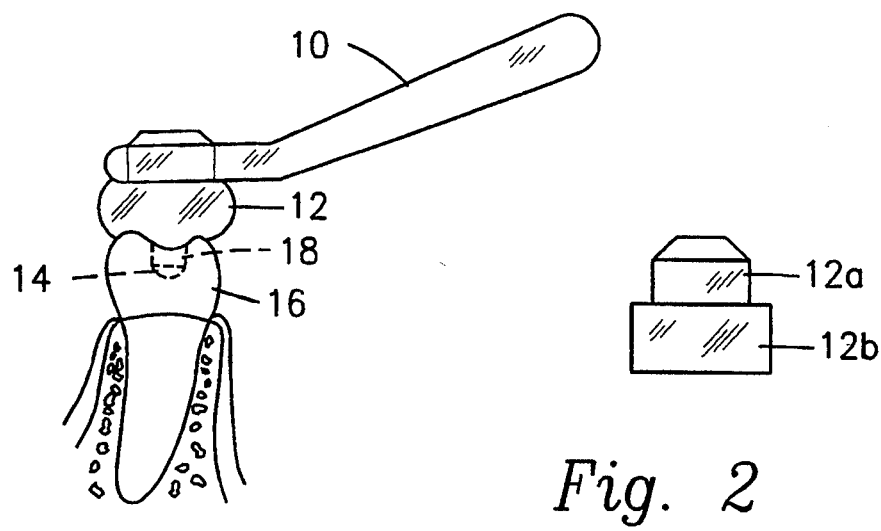
Fig. 1
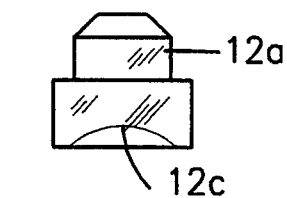
Fig. 2
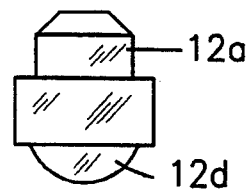
Fig. 3
Fig. 4
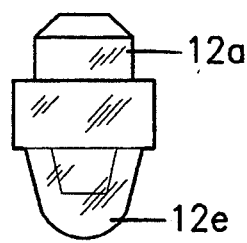
Fig. 5
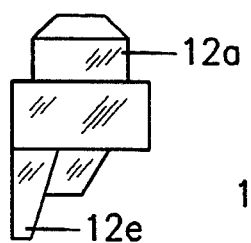
Fig. 6
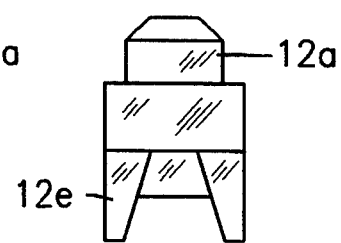
Fig. 7

APPARATUS FOR COMPRESSING AND ADAPTING FILLING MATERIAL

BACKGROUND OF THE INVENTION

The invention relates to an apparatus for compressing and adapting the plastic filling or stopping material introduced into a dental cavity.

Contact with the cavity wall is of decisive importance for the quality and durability of a filling. With the presently conventional tamping of the plastic, more or less adhesive filling material, marginal gaps and vacuoles can be left behind, because after tamping the instrument must be withdrawn. However, fillings must completely harden under pressure.

DE 40 10 857 C1 discloses an apparatus improving the application procedure for prepared inlays. This apparatus is not advantageous for the compression of a plastic filling material.

DE 77 19 858 U discloses a screen which surrounds the exit aperture of a light guide and therefore protects the operator by preventing peripheral light leakage.

U.S. Pat. No. 5,098,292 discloses an apparatus for the curing of the deeper layers of plastic filling material introduced into a cavity from a rigid, light-conducting tip.

EP 169 803 discloses an apparatus for the light-curing of filling material. It consists of rigid, light-conducting wedges, which are inserted between two adjacent teeth.

SUMMARY OF THE INVENTION

The problem of the invention is to provide an apparatus, which can adapt to the given rigid tooth surface, but can fluid compress and model the yielding, i.e., still plastic parts and can therefore adapt to the surrounding area.

According to the invention, this problem is solved by an elastic punch, which is fixed in or on a holder.

The punch is preferable formed from a holding portion and an adapting portion to be pressed onto the tooth or cavity. The surface of the adapting portion to be engaged on the tooth can be planar, but can also be provided with a depression or a protuberance.

It has proved particularly appropriate to construct the punch with a Shore hardness between 15 and 50. The Shore hardness to be chosen is dependent on the filling or stopping material used. As frequently light-hardening filling materials are used, the punch and the holder should be made from a transparent material.

DESCRIPTION OF THE DRAWINGS

The invention is described in greater detail hereinafter relative to non-limitative embodiments and the attached drawings, wherein show:

FIG. 1 is a perspective view of the punch apparatus.
FIG. 2 is a first embodiment of the punch in a side elevational view.
FIG. 3 is a second embodiment of the punch in a side elevational view.
FIG. 4 is a third embodiment of the punch in a side elevational view.
FIG. 5 is a fourth embodiment of the punch in a side elevational view with one or two terminal extensions.
FIG. 6 is the fourth embodiment of the punch in a front elevational view with a terminal extension.
FIG. 7 is a fourth embodiment of the punch in a front elevational view with two terminal extensions.

DETAILED DESCRIPTION OF THE PREFERRED EMBODIMENTS

Figure 8:
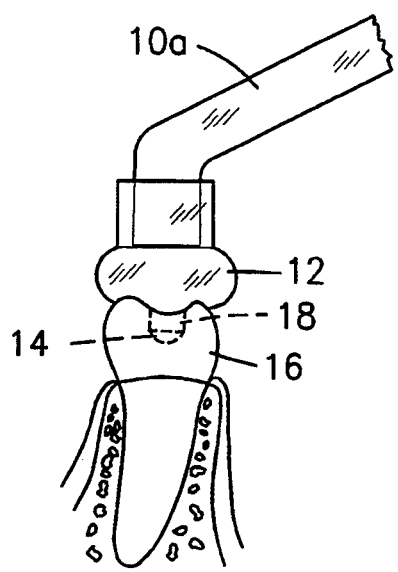
FIG. 8 is the punch apparatus according to FIG. 1 with a holder centrally inserted in the punch.

Throughout the following detailed description, the same reference numerals refer to the same elements in all figures.

The apparatus for compressing and adapting the plastic material introduced into a cavity 14 of a tooth 16 in FIG. 1 comprises an elastic punch 12, which can be fixed in a holder 10. The Shore hardness of the punch 12 is between 15 and 50.

In the embodiment shown in FIG. 2, the surface of the adapting portion 12b to be engaged on the cavity 14 is planar.

In the embodiment shown in FIG. 3, the surface of the adapting portion 12c to be engaged on the cavity 14 is constructed with a slightly concave depression.

In the embodiment of FIG. 4, the surface of the adapting portion 12d to be engaged on the cavity 14 is constructed with a slightly convex protuberance.

When using the apparatus, the punch 12 is pressed onto the filling material 18 introduced into the cavity 14, the punch elasticity ensuring a uniform force application. This brings about a reliable edge closure between the filling material and the cavity wall, vacuoles being avoided.

Due to the considerable adaption width, regularly the punch 12 shown in FIG. 1 can be used with a planar base surface 12b. However, with young patients having a large process height, it can be advantageous to use the punch shown in FIG. 4, which has in the embodiment shown, a substantially frustum shaped protuberance 12d, which leads to a higher central pressure.

The punch 12 shown in FIG. 3 and provided with a depression 12c is mainly used in the case of cavities in the lateral faces. The all-round edge serves to provide a complete seal and creates the necessary contact with the reference surface.

The punch 12 shown in FIGS. 5, 6 and 7 is provided with terminal extensions used mainly for occlusal-approximal cavities.

Figure 9:
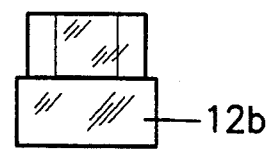
FIG. 9 is the punch according to FIG. 2 with a holder centrally inserted in the punch.
Figure 10:
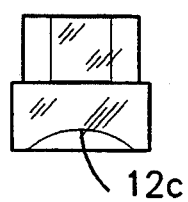
FIG. 10 is the punch according to FIG. 3 with a holder centrally inserted in the punch.
Figure 11:
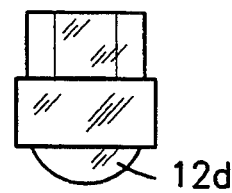
FIG. 11 is the punch according to FIG. 4 with a holder centrally inserted in the punch.

The FIGS. 8 to 11 are similar to the FIGS. 1 to 4, except the holder 10a inserts centrally in the punch 12.

When using a light-hardening filling material, the punch 12 and the holder 10 are made from a transparent material and are therefore light conductive.

I claim:

1. An apparatus for compressing a light-hardening filling in a dental activity comprising,
    an elastomeric transparent punch having a bottom portion attached to a top adaptor portion, the bottom portion having a bottom surface, and
    a rigid transparent holder adapted to be held by a dentist, the rigid holder having an aperture formed at an end portion for receiving the adapter portion of the punch, the adaptor portion frictionally mounted in the aperture.

2. An apparatus according to claim 1 wherein the bottom surface of the bottom portion of the punch is planar.

3. An apparatus according to claim 1 wherein the bottom surface of the bottom portion of the punch is concave.

4. An apparatus according to claim 1 wherein the bottom surface of the bottom portion of the punch has a convex protuberance.

5. An apparatus according to claim 4 wherein the protuberance is frustum shaped.

6. An apparatus according to claim 5 wherein the frustum shaped protuberance has a terminal extension on at least one side.

7. An apparatus according to claim 5 wherein the frustum shaped protuberance has two terminal extensions.

8. An apparatus according to claim 1 wherein the punch has a Shore hardness of between 15 and 50.

* * * * *